United States Patent [19]
Nelson et al.

[11] Patent Number: 5,219,332
[45] Date of Patent: Jun. 15, 1993

[54] ROTATION TOOL FOR MEDICAL GUIDEWIRE

[75] Inventors: Arlin D. Nelson, Midvale; Fred P. Lampropoulos, Salt Lake City, both of Utah

[73] Assignee: Merit Medical Systems, Inc., Salt Lake City, Utah

[21] Appl. No.: 984,227

[22] Filed: Nov. 30, 1992

[51] Int. Cl.$^5$ ............................................ A61B 5/00
[52] U.S. Cl. ............................... 604/95; 604/159; 128/657; 128/772
[58] Field of Search .............. 604/280, 283, 95, 159, 604/165, 170, 249, 250; 128/656, 657, 658, 772; 606/1; 226/127, 158, 162

[56] References Cited

U.S. PATENT DOCUMENTS

| | | | |
|---|---|---|---|
| 4,799,496 | 1/1989 | Hargreaves et al. | 128/772 |
| 4,858,810 | 8/1989 | Intlekofer et al. | 604/159 X |
| 4,957,117 | 9/1990 | Wysham | 604/95 |
| 5,137,288 | 8/1992 | Starkey et al. | 604/159 X |
| 5,137,517 | 8/1992 | Loney et al. | 604/159 |
| 5,161,534 | 11/1992 | Berthiaume | 604/159 X |

Primary Examiner—John D. Yasko
Attorney, Agent, or Firm—Workman Nydegger Jensen

[57] ABSTRACT

A gripping-knob rotation tool for attachment to a medical guidewire as used in angioplasty and other medical procedures. The tool is installed laterally over the guidewire at any desired position along the length of the wire, and is secured thereto by a simple rotational or twisting motion. The tool provides a convenient gripping surface during rotation or translational movement of the guidewire, and is adjustable for repositioning along the length of the wire after initial engagement.

27 Claims, 11 Drawing Sheets

ROTATION TOOL FOR MEDICAL GUIDEWIRE

BACKGROUND

1. Field of the Invention

This invention relates to a knob-like tool for attachment to a medical guidewire as used, for example, to guide a catheter into an artery or arterial branch to a stenosis or partial blockage position where vessel enlargement is performed with an angioplasty balloon.

2. The Prior State of the Art

The use of guidewires in catheterization and angioplasty procedures is well known, and is further described in issued patents such as U.S. Pat. No. 4,957,117.

The guidewire is long (typically six feet or more of stainless steel wire) and slender with a relatively limber and bendable distal tip which can be angled to assist the physician in negotiating arterial curves and junctions to the desired location by fluoroscopic monitoring.

The surface of the slender guidewire is smooth and slick, and some kind of auxiliary gripping surface is needed to enable the wire to be advanced into or retracted from the arterial vessels, and especially to enable twisting or torquing rotation of the wire as needed to reorient the angled distal tip. Existing partial solutions to this need include pin-vise grips.

A pin-vise is a device that is well known in the art and which comprises a structure like a small drill chuck with a cylindrical handle. The chuck is threaded over the proximal end of the long guidewire and advanced to a desired position. A chuck collet, a part of the pin-vise, can then be tightened onto the wire so that the pin-vise is firmly attached to the guidewire, and thereafter serves as a grip to facilitate manual rotation of the guidewire and/or longitudinal advancement of the same.

One of the problems which has been experienced in the art using pin-vise type grips is that they must be threaded onto the guidewire at the proximal end. This is time consuming and inconvenient because of the length of the guidewire. Thus, other types of gripping devices have been devised which attempt to overcome this problem.

One such gripping device is illustrated, for example, in U.S. Pat. No. 4,829,999. This device is constructed with a cylindrical body which has a longitudinal slit and which is spring-actuated so that by pressing two handles together which are provided on the body of the device, the longitudinal slit can be opened and placed onto the guidewire. When the handles are released, the resilient or spring-action of the cylindrical body clamps the guidewire within the longitudinal slit, much like clamping a clothespin into a clothesline.

This device overcomes the problem of having to thread the device onto the proximal end of the guidewire, but suffers from other disadvantages. For example, the handles which are located on the side of the cylindrical body may get in the way of rotational manipulation of the device. Furthermore, it is typically necessary to reposition a gripping device on a guidewire as the guidewire is advanced further into the vessels. Thus, the side mount type gripping device as described for example in the above referenced patent requires that the device be taken off and repositioned on the guidewire. If the device is dropped while taking it off, it becomes unsterile and must be replaced.

Another device which has attempted to address the problems in the art is illustrated, for example, in U.S. Pat. No. 4,858,810. This device utilizes a pin-vise constructed from two parts assembled together to provide a gripping handle for a guidewire. The device has an elongated cylindrical body which is slotted along the length to receive the guidewire, and also has a sliding mechanism which fits within the slot and which, when pushed forward, tightens down upon the guidewire in order to secure the gripping device to the guidewire for purposes of manipulation. As in the case of the spring-actuated type gripping device described above, this device is also a side-mount type device, which eliminates the need for threading the device onto the proximal end of the guidewire. However, the placement of the device onto the guidewire is somewhat cumbersome and if the cylindrical body member is inadvertently dropped before the slide mechanism is placed into the longitudinal slot, once again the device may become unsterile. Another example of a device that utilizes a slide mechanism is that described in U.S. Pat. No. 5,159,861.

Still a further device which is known in the art is a side loading type of gripping device which, once again, employs a longitudinal slot along the length of the device, and which includes two cylindrical members that are threaded together. The distal end of one of the cylindrical members is formed with a plurality of fingers so that as the two members are threaded together the fingers clamp down and grip the guidewire. This device, like the others, partially solves some of the problems experienced in the art, but is otherwise more complicated in its construction and cumbersome to operate than is desirable.

SUMMARY AND OBJECTS OF THE INVENTION

The rotation tool of this invention overcomes the above and other problems in the art, and enables quick and simple lateral or sideways attachment at any desired position along a guidewire. The tool further provides two gripping modes, one in which the guidewire is captive within the tool, so that the tool cannot fall off the guidewire, but the guidewire is otherwise not longitudinally or rotationally secured to the tool so that relative movement of the tool on the guidewire is permitted. The second gripping mode is one in which the guidewire is secured to the rotation tool, both longitudinally and rotationally so that the rotation tool can be used either to advance the guidewire or to rotationally orient the guidewire to effect steering of the distal end of the guidewire.

In one presently preferred embodiment of the invention, the rotation tool is comprised of a tubular housing that is formed from two cylindrical members that are adapted to fit together in a telescoping arrangement. The two members are provided with a passageway that runs through the length of each member. A slot also runs the length of each member and extends from an outer surface of each member to the passageway running therethrough. An elastomeric gripping and retention member has one end anchored in one of the cylindrical members and the other end anchored in the other cylindrical member at the ends of the passageways formed through the cylindrical members. An elongated body of the elastomeric member is situated in the passageway running between the two ends.

The guidewire is placed into the longitudinal slot and the two cylindrical members can then be rotated relative to each other to a first position which locks the guidewire within the device, but without securing the guidewire to the device. In this position, the rotation tool or device of the present invention is in the first gripping mode described above. The cylindrical members can then be rotated to a second position which causes the elastomeric member to twist around the guidewire, but without bending the guidewire. When locked in this second position, the rotation tool or device of the present invention is in the second gripping mode described above.

It is therefore an object of the present invention to provide a rotation tool for attachment to a guidewire which overcomes the above and other problems which have been experienced in the present state of the art.

More specifically, it is an object of the present invention to provide a rotation tool for attachment to a medical guidewire which is simple and inexpensive in its construction and assembly, and which can be positioned onto a guidewire at any point along the length of the guidewire so as to eliminate the necessity for threading the tool onto the proximal end of the guidewire.

Yet a further object of the present invention is to provide a rotation tool for attachment to a medical guidewire which provides for two gripping modes, one in which the device is locked onto the guidewire but can be moved relative to the guidewire so that the guidewire is not longitudinally or rotationally gripped by the device, but the device is nonetheless prevented from falling off of the guidewire, and a second gripping mode in which the device is locked to the guidewire both longitudinally and rotationally to permit the guidewire to be steered at its distal end by manipulation of the tool.

These and other objects and features of the present invention will become more fully understood from reference to the accompanying drawings which are briefly summarized below and which are used to illustrate one presently preferred embodiment of the invention in its presently understood best mode for making and using the same.

DETAILED DESCRIPTION OF THE PREFERRED EMBODIMENT

Figure 1:
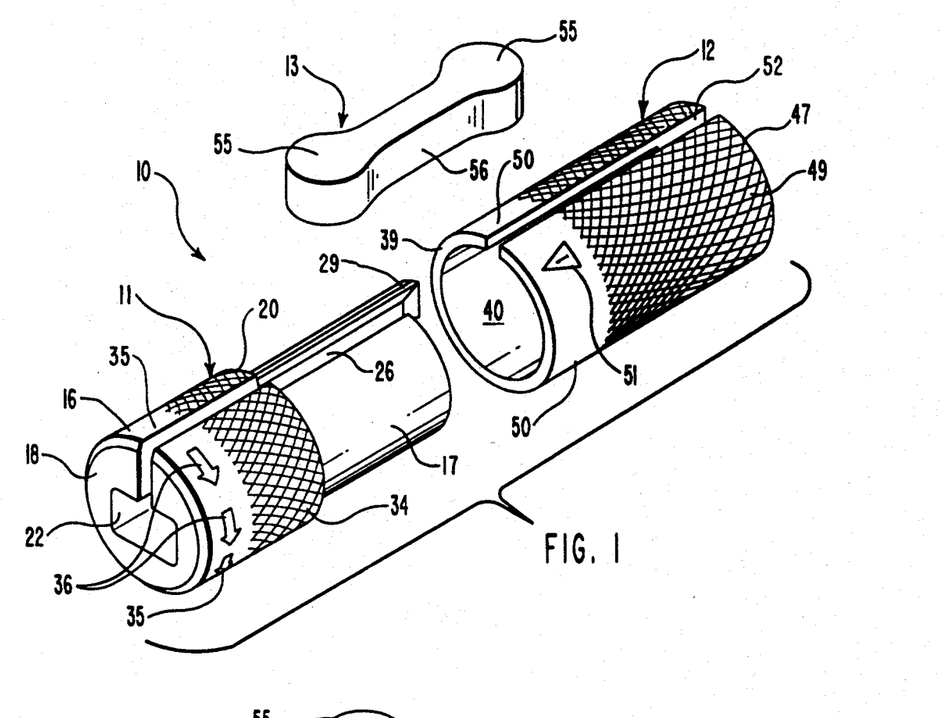
FIGS. 1 and 2 are exploded pictorial views showing a pair of tubular members and an elastomeric retainer which comprise a preferred embodiment of this invention.
Figure 2:
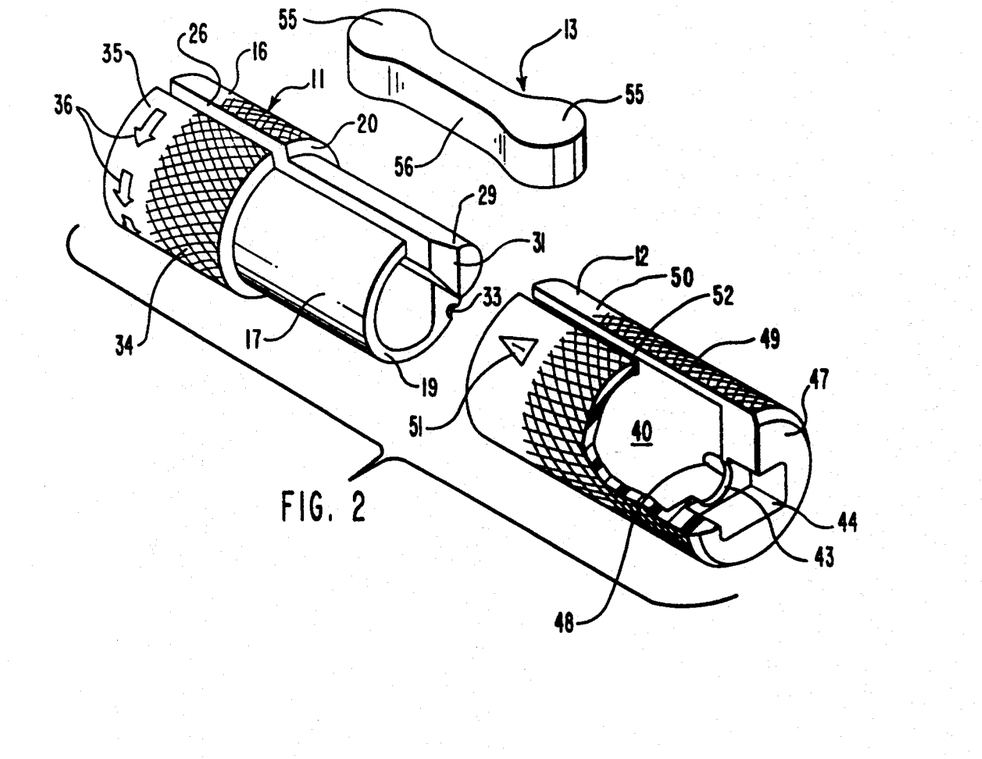
Figure 3:
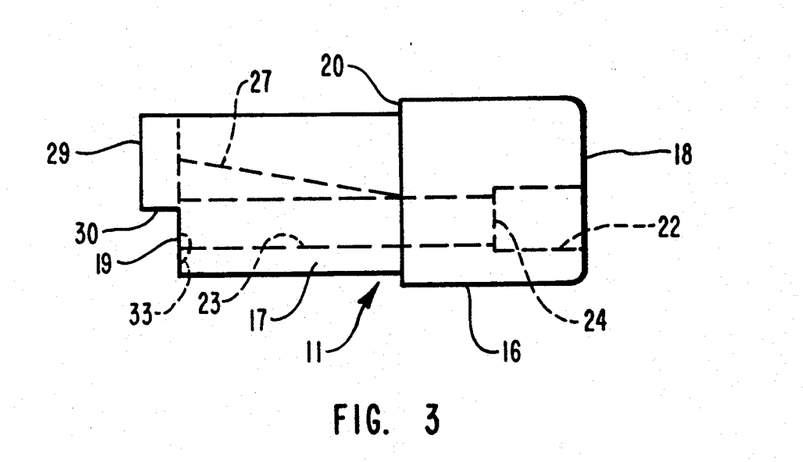
FIG. 3 is a side elevation of a first tubular member.
Figure 14:
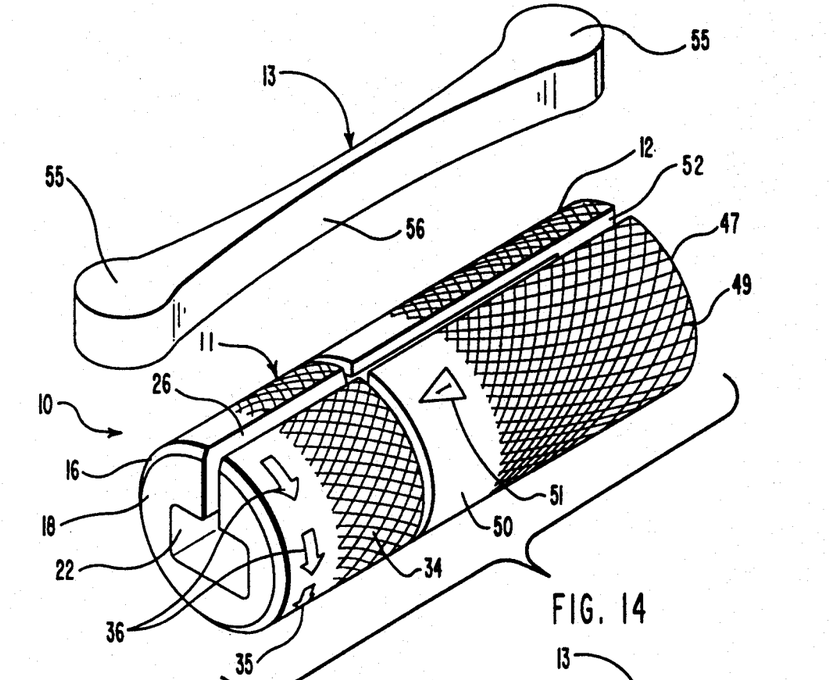
FIG. 14 is a pictorial view of the engaged tubular members, and showing the elastomeric member in a stretched position ready for installation.
Figure 15:
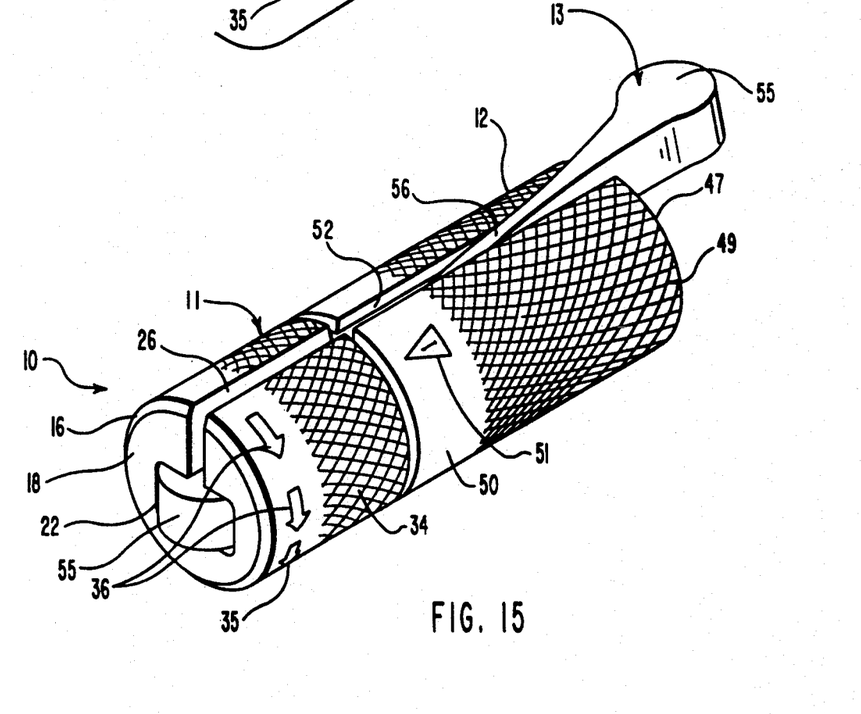
FIG. 15 shows the partially installed elastomeric member.

The components of a rotation tool or gripping-knob assembly 10 are shown in exploded view in FIGS. 1 and 2. The components are a first tubular plug member generally designated at 11, a mating second tubular socket member generally designated at 12, and an elastomeric retainer generally designated at 13. The steps of assembling the tool are shown in FIG. 14-15, and the assembled tool is shown as placed over and engaged with a medical guidewire 14 in FIGS. 16-23. The details of each component will first be described, and subsequently the assembly and use of the tool.

Referring to FIGS. 1-9, a first tubular member 11 has a cylindrical head 16, a coaxial cylindrical shank 17 extending from the head, a head end surface 18, and a shank end surface 19. The shank has a slightly reduced diameter as compared to the head, and the respective diameters are typically about 0.455 inch and 0.352 inch. An annular shoulder 20 is defined at the junction of the head 16 and shank 17.

A rectangular-in-cross-section recess 22 extends into head 16 from end surface 18 part way toward shoulder 20. As shown best in FIGS. 3–6, a cylindrical bore or passageway 23 extends from a base 24 of recess 22 to shank end surface 19. Passageway 23 has a typical diameter of 0.12 inch, and an axial centerline which is parallel to, but offset by slightly less than the radius of the passageway 23 from the axial centerline of the head 16 and shank 17.

Figure 5:
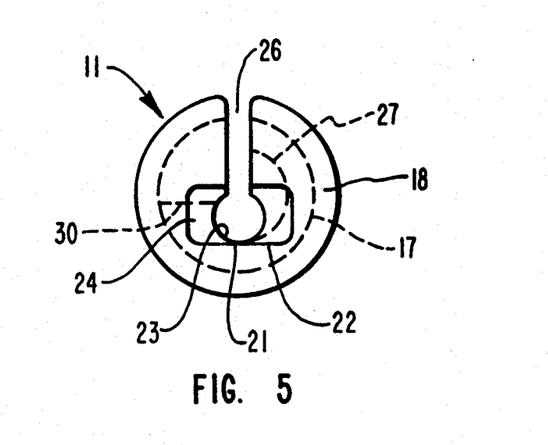
FIG. 5 is an end view of one end of the first tubular member shown in FIG. 3.
Figure 6:
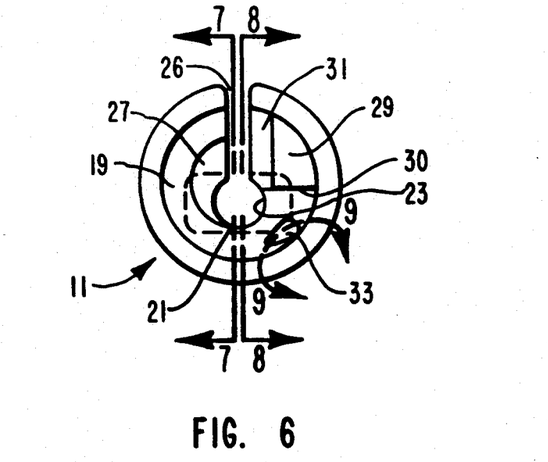
FIG. 6 is an opposite end view of the first tubular member of FIG. 3.
Figure 7:
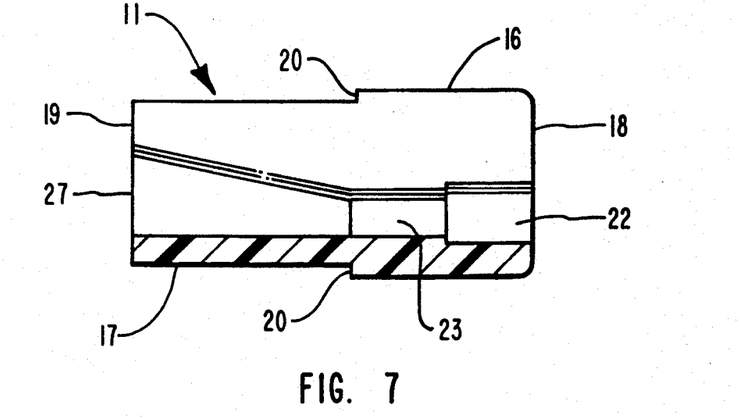
FIG. 7 is a sectional side elevation on line 7—7 of FIG. 6.
Figure 8:
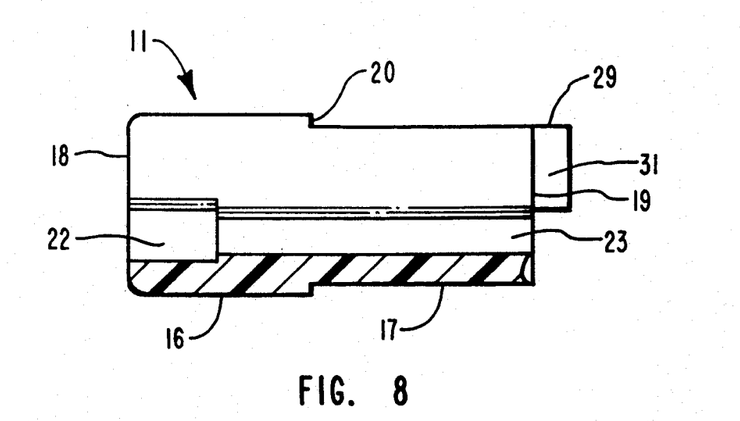
FIG. 8 is a sectional side elevation on line 8—8 of FIG. 6.

A slot 26 (shown best in FIGS. 1-2 and 5-6) extends from recess 22 and passageway 23 radially outwardly to the outer surfaces of the head 16 and shank 17, and extends the full length of member 11 between end surfaces 18 and 19. A semiconical recess 27 (FIGS. 3 and 5) is concentric with the head 16 and shank 17, and converges from end surface 19 to terminate at passageway 23 adjacent shoulder 20. Recess 27 is formed in only one inner side of the shank 17, and the nearly semicircular outer perimeter of the recess 27 extends from a sidewall of slot 26 to terminate at a point of tangency 21 with the lower (as seen in FIG. 5-6) perimeter of passageway 23.

Figure 4:
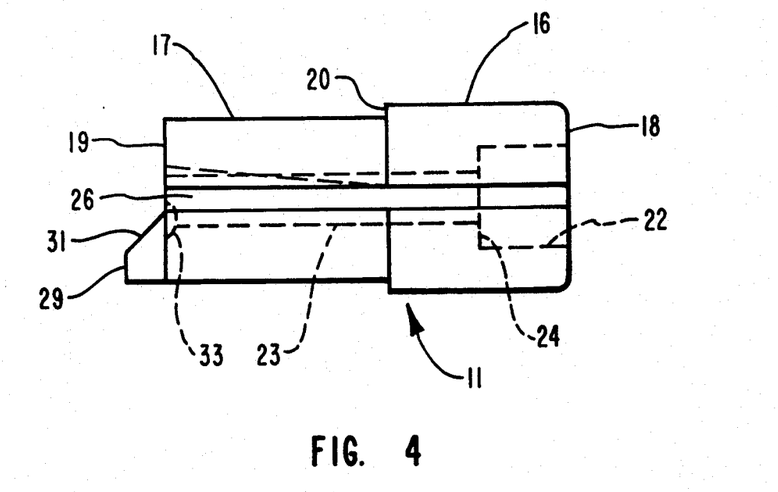
FIG. 4 is a top view of the first tubular member shown in FIG. 3.
Figure 9:
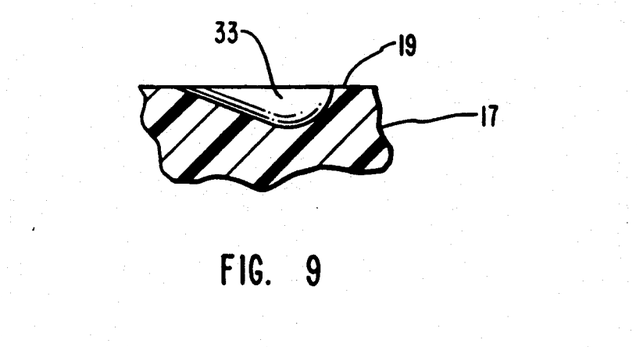
FIG. 9 is an enlarged partial sectional view on line 9—9 of FIG. 6 and showing a detent seat.
Figure 10:
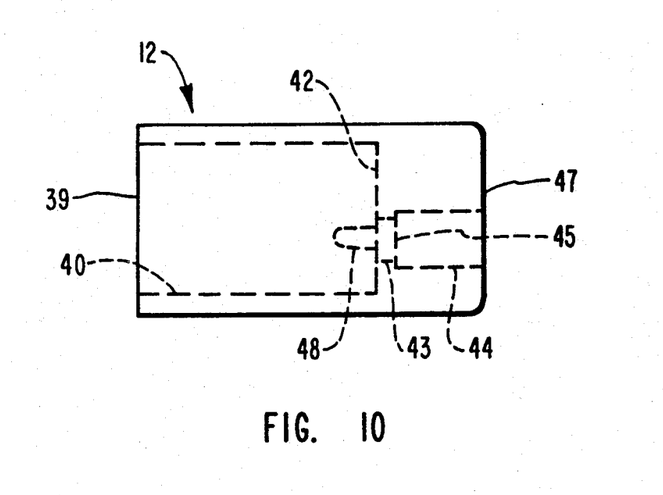
FIG. 10 is a side elevation of a second tubular member.
Figure 11:
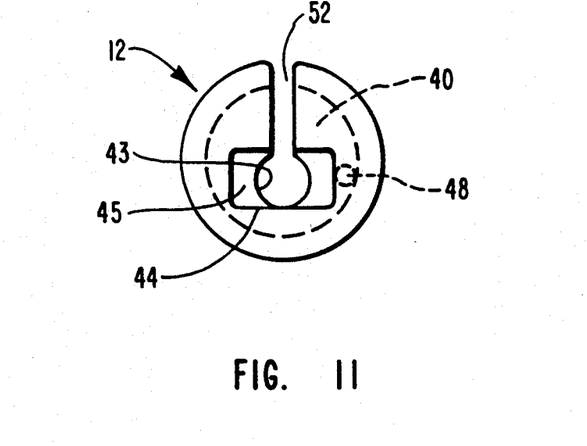
FIG. 11 is an end view of one end of the second tubular member of FIG. 10.
Figure 12:
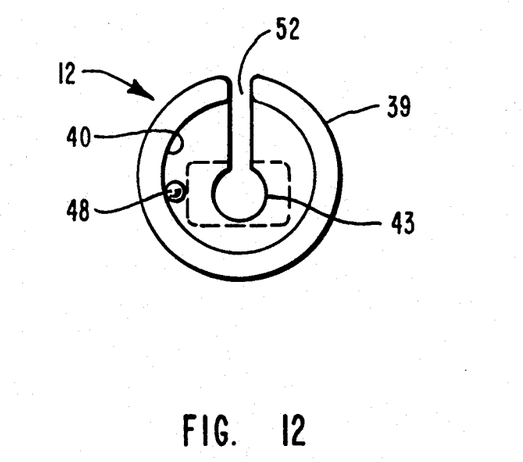
FIG. 12 is an opposite end view of the second tubular member.

An extension protrudes from shank end surface 19 to define a stop 29 with a shoulder 30 (see FIG. 3) extending from passageway 23 to the outer surface of cylindrical shank 17. The stop 29 has a chamfered surface 31 adjacent slot 26 as best seen in FIGS. 2 and 4. A teardrop-shaped detent seat 33 is formed as a depression in end surface 19 below shoulder 30 (as shown in FIGS. 2, 6 and 9) and adjacent the perimeter of shank 17. A preferred cross-sectional shape of seat 33 is shown in FIG. 9, and the blunt end of the seat 33 is positioned about 54 degrees counterclockwise from the six o'clock position in FIG. 6.

The outer surface of cylindrical head 16 has a knurled portion 34 (FIGS. 1-2) for secure gripping, and a smooth portion 35 surrounding recess 22. The smooth portion 35 is embossed with arrows 36 designating the proper rotation direction to turn plug member 11 to engage assembly 10 with guidewire 14 as explained below in greater detail.

Tubular socket member 12 is shown in detail in FIGS. 1-2 and 10-13, and is generally cylindrical in shape with first and second ends 39 and 47. A coaxial cylindrical bore 40 extends from first end 39 to a base surface 42 (see FIG. 10) axially spaced from the second end 47. Bore 40 is dimensioned to receive shank 17 of the tubular plug member 11 in rotatable engagement, and has a typical inside diameter of 0.356 inch for a shank outside diameter of 0.352 inch. An off-axis cylindrical bore or passageway 43 (FIGS. 10-11) extends from surface 42 to a rectangular recess 44 which is identical to recess 22. The recess 44 has a base 45, and extends axially to second end 47.

A slot 52 is formed in socket member 12 between ends 39 and 47, and extends from the outer surface of the member radially inward to bore 40, passageway 43 and recess 44. A detent pin 48 extends from base surface 42, and is positioned adjacent the inner surface of bore 40, passageway 43 and recess 44. The detent pin 48 is positioned adjacent the inner surface of bore 40 about 110 degrees counterclockwise from the twelve o'clock position in FIG. 11. The pin 48 is preferably integrally formed with member 12, and is slightly tapered for molding convenience, and for structural strength at the pin base.

Figure 20:
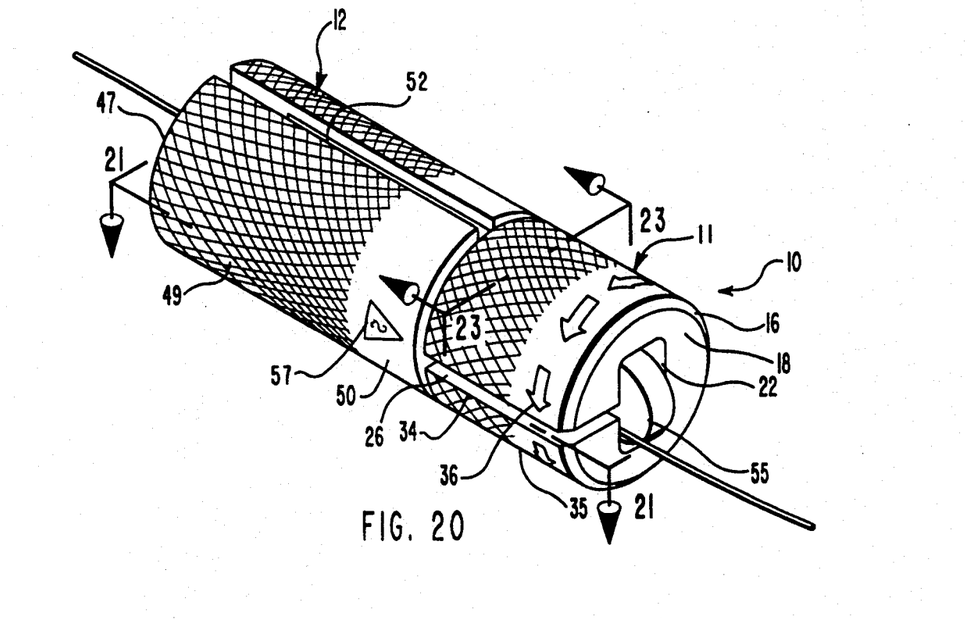
FIG. 20 shows the tubular members from a different angle, and rotated to a locked position in which the guidewire is longitudinally and rotationally secured relative to the tool.
Figure 21:
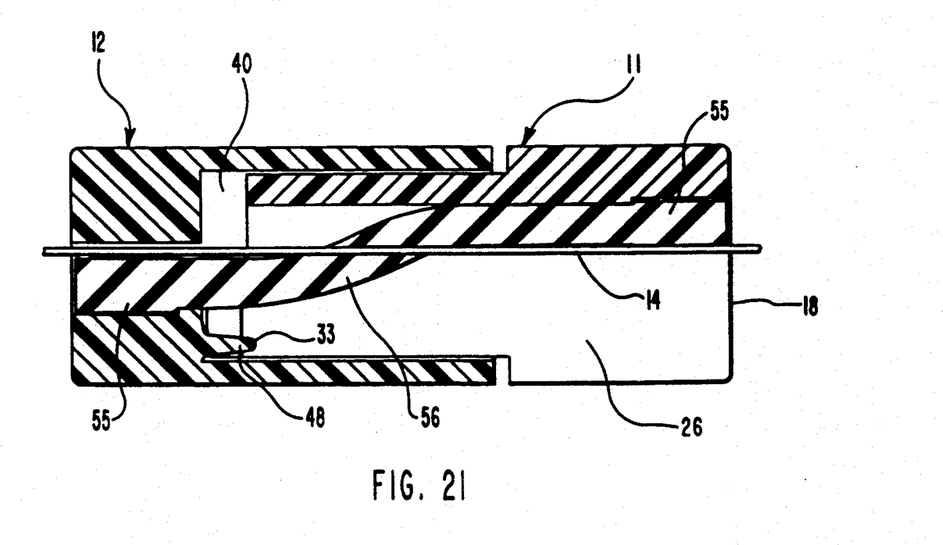
FIG. 21 is a sectional side elevation taken on line 21—21 of FIG. 20, and more particularly showing the relationship of the elastomeric member and the guidewire when the first and second tubular members are rotated to the second position.
Figure 22:
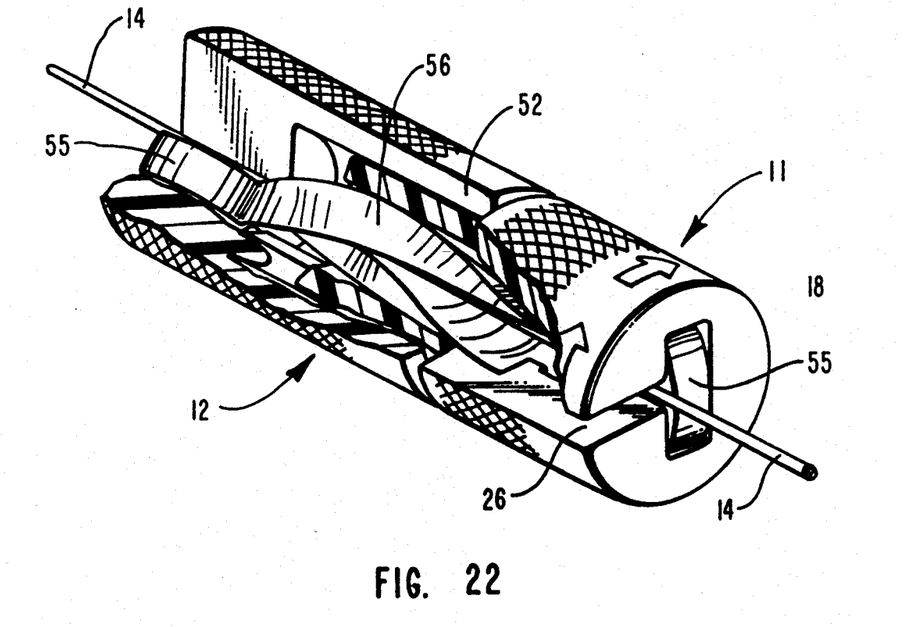
FIG. 22 is a perspective view with portions broken away to further illustrate the relationship between the elastomeric member and guidewire when the first and second tubular members are rotated to the second position.
Figure 23:
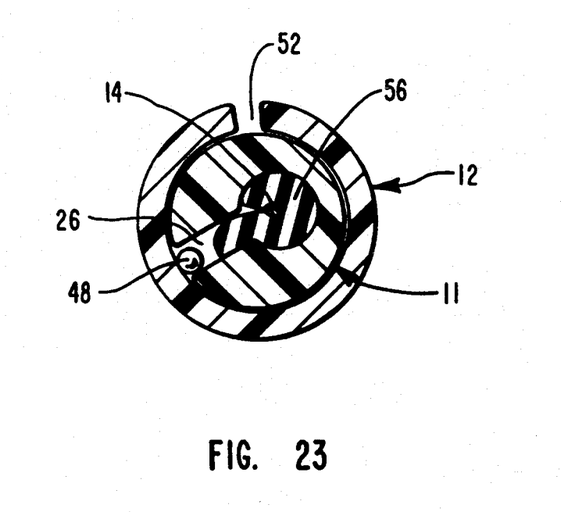
FIG. 23 is a sectional view taken on line 23—23 of FIG. 20 which further illustrates the relationship between the guidewire and the elastomeric member when the first and second tubular members are rotated to the second position.

Referring to FIGS. 1-2, the outer surface of member 12 has a knurled gripping portion 49, and a smooth portion 50 in which are embossed a pair of first and second position markers 51 and 57 (the latter is shown in FIG. 20). When members 11 and 12 are engaged, markers 51 and 52 are alternatively aligned with slot 26 of the plug member 11 in the several operational positions of the assembly as described below.

Elastomer retainer 13 is best seen in FIGS. 1-2 and 14-15, and is an integral member having enlarged circular heads 55 at its opposite ends. Heads 55 are dimensioned to seat securely in recesses 22 and 44 when assembled with plug and socket members 11 and 12. The heads 55 are connected by a body member 56 which is rectangular in cross section. The body member 56 is intended to fill a substantial portion of passageways 23 and 43 when assembled with the plug and socket members. For example, if the passageways 23 and 43 have matching diameters of about 0.12 inch, the cross-sectional dimensions of body member 56 are preferably about 0.10 and 0.15 inch.

Retainer 13 is preferably molded from neoprene or silicone rubber with a Shore A hardness of about 55. Plug and socket members 11 and 12 are preferably each integrally injection molded for economy and production convenience, and a suitable material is ABS plastic.

Figure 13:
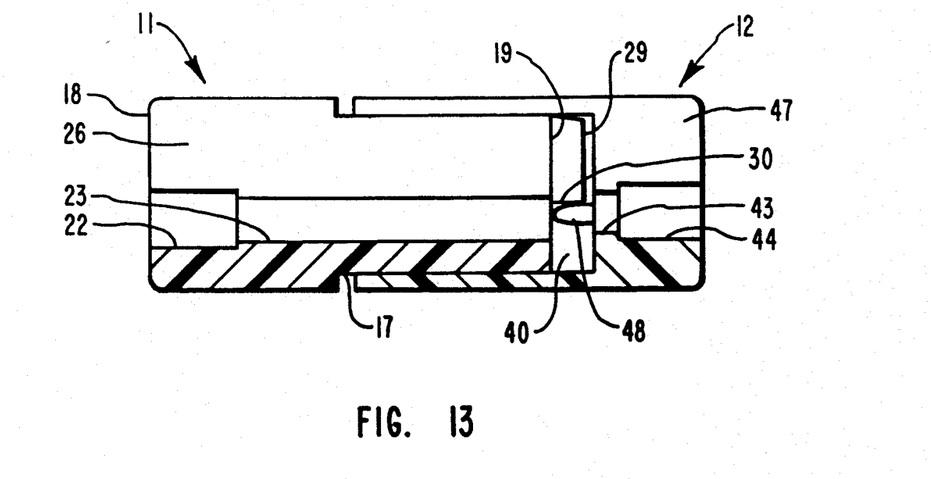
FIG. 13 is a sectional side elevation showing the first and second tubular members as assembled together.

The assembly of the several components just described is shown in FIGS. 13-15. As shown best in FIG. 13, the shank 17 of plug member 11 is inserted into bore 40 of the socket member 12 until the end 19 of shank 17 abuts against pin 48. Radial slots 26 and 52 are in alignment as shown in FIG. 14.

Body member 56 is then tensioned to elongate retainer 13 as shown in FIG. 14, and the body member 56 is fitted into aligned slots 26 and 52 to seat one of retainer heads 55 in rectangular recess 22 of the plug member 11 (FIG. 15). The still-elongated body member 56 is then fully fitted through slots 26 and 52 into passages 23 and 43, and the second head 55 is seated in recess 44 of the socket member 12. In this fully assembled condition, body member 56 remains under substantial tension, and the resulting restoring force urges the plug and socket members 11 and 12 together.

Figure 16:
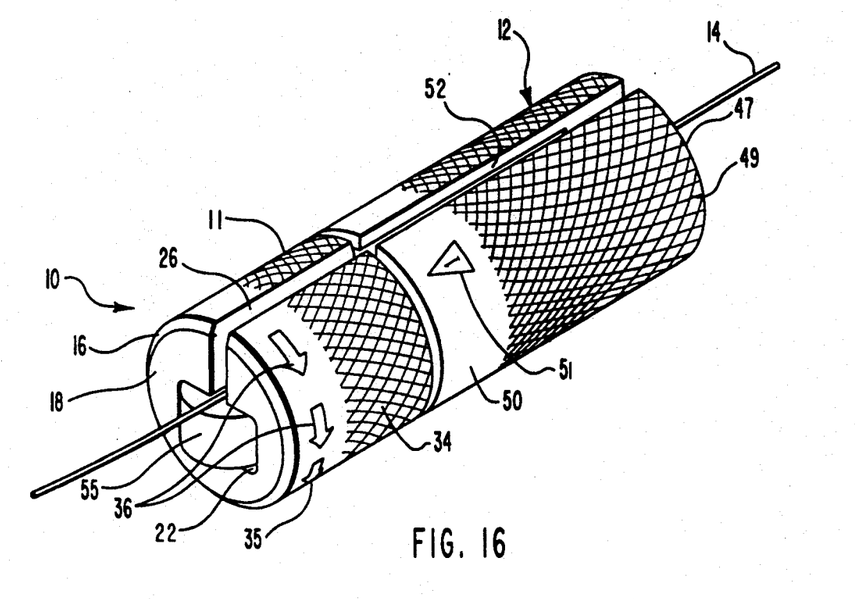
FIG. 16 shows the completely assembled tool with a guidewire in an initial position.
Figure 17:
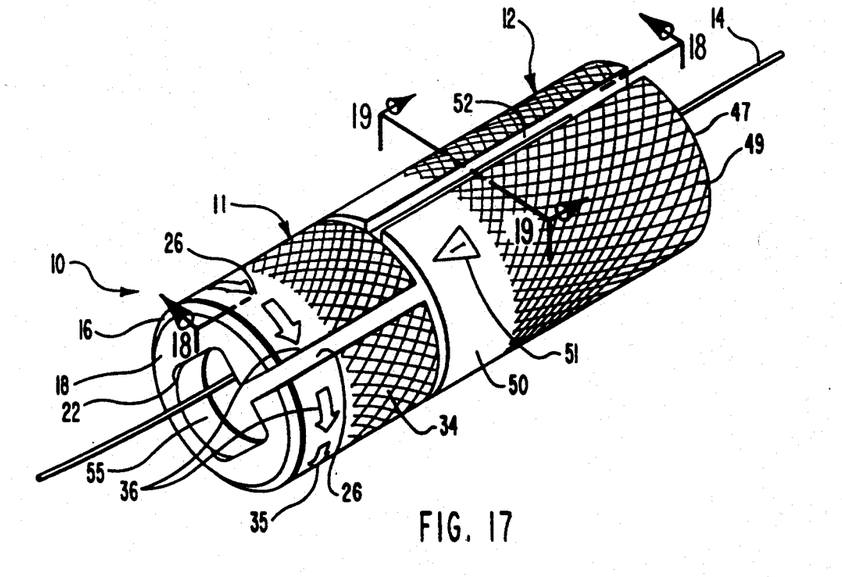
FIG. 17 shows the tubular members rotated to a first position which makes the guidewire captive, but longitudinally and rotationally free within the tool.
Figure 18:
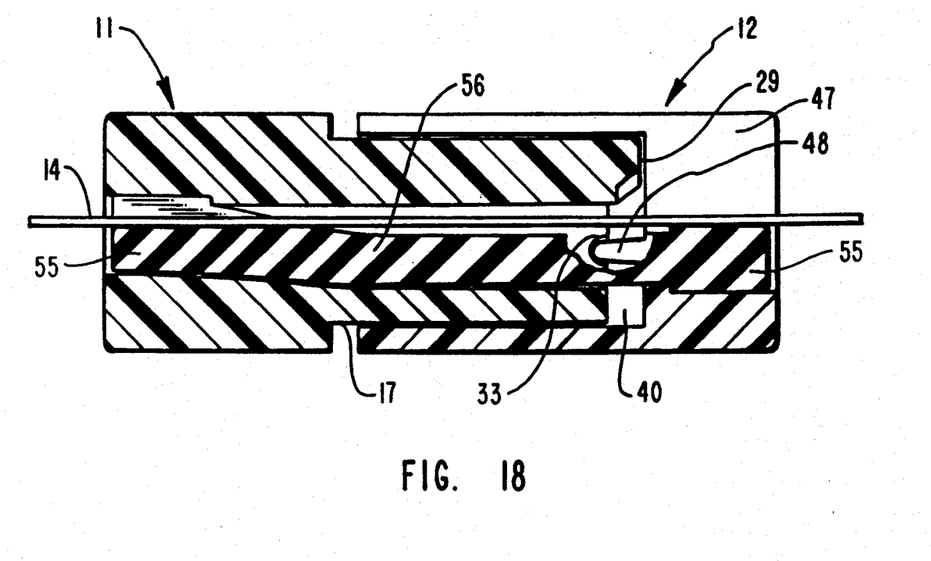
FIG. 18 is a longitudinal cross-sectional view taken on line 18—18 of FIG. 17, and more particularly shows the relationship between the elastomeric member and the guidewire when the tubular members are rotated to the first position.
Figure 19:
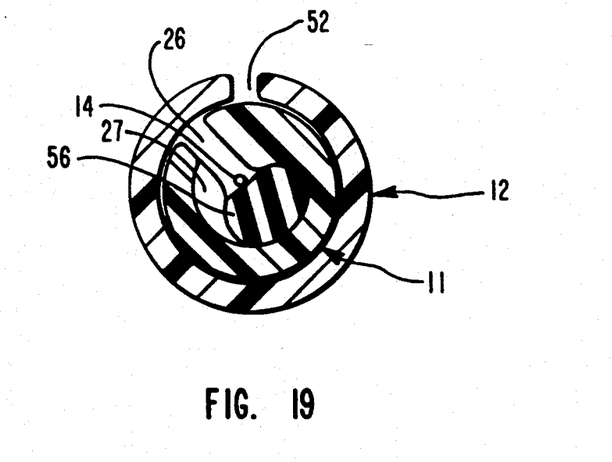
FIG. 19 is a cross-sectional view taken on line 19—19 of FIG. 17 further showing the relationship between the elastomeric member and the guidewire when the tubular members are rotated into the first position.

Initial engagement of the device 10 over guidewire 14 is illustrated in FIG. 16. The device is simply moved laterally over the guidewire 14 which passes through aligned slots 26 and 52 to rest against retainer 13. Plug member 11 is then rotated about 25 degrees in the direction of arrows 36 to an intermediate position (FIGS. 17-19) in which detent pin 48 moves into seat 33. Because of the tension exerted by retainer 13, the seating of the pin 48 into seat 33 occurs with a click so as to give an audible and a tactile signal that the intermediate position has been reached, and visual confirmation is also provided by the alignment of slot 26 with first position markers 51. As shown best in FIGS. 18-19, in the intermediate position, the guidewire 14 is captive within the shank 17 of socket member 11 by the misalignment of slots 26 and 52, but is not secured by the body member 56 of retainer 13, which is only slightly twisted in this position, thus device 10, permitting longitudinal repositioning of the device along the guidewire 14 without having to remove it from guidewire 14.

To lock the device 10 to the guidewire 14 both longitudinally and rotationally, the plug and socket members 11 and 12 are lightly separated against the force of the tensioned retainer 13 to move detent pin 48 out of seat 33. The plug member is then rotated in the direction of arrows 36 by about 225 degrees to the final position as shown in FIGS. 20-23. Pin 48 rides along shank end surface 19 during this rotational movement, and provides a tactile signal of reaching the final position, again due to the tension exerted by retainer 13, by dropping into the shank end of radial slot 26. Visual confirmation of this position is provided by the alignment of slot 26 with second position marker 52, and further rotation is discouraged by stop 29.

Relative rotation of the plug and socket members 11 and 12 to this position twists the retainer 13 within the passageways 23, 27 and 43, and the guidewire 14 is thus gripped and secured by the body member 56 as it twists about guidewire 14. The semiconical recess 27 (see FIGS. 3 and 6) provides space for the body member 56 of retainer 13 to be twisted up and around guidewire 14, without bending the guidewire. Importantly, guidewire 14 is not bent so that rotation of device 10 results in a corresponding rotation at the distal end of guidewire 14 in the vessel. The conical passageway 27 in shank 17 permits the body member 56 of retainer 13 to twist up and around guidewire 14 to securely grip it. This is shown best in FIGS. 21-23. Guidewire 14 is thus now secured by device 10 to permit both longitudinal and/or rotational manipulation of guidewire 14 by manipulating the tool or device 10.

The central axis of passageways 23 and 43 are intentionally spaced from the common rotation axis of the plug and socket members to insure that after body member 56 is seated in passageways 23 and 43, the guidewire will come to rest on body member 56 (see FIGS. 18 and 19) in substantial alignment with the common rotation axis. This feature avoids the undesirable result of the guidewire extending from the assembly at an angle or off-centered axis which would result in inconvenient operation.

The design of the device permits quick and simple lateral or sideways installation at any position along the guidewire 14, and the rotational alignment of the plug and socket members 11 and 12 is easily determined either visually or by tactile feel when the detent pin 48 moves into a partially or fully retained position. Should it be necessary to reposition the assembly during advancement of the guidewire 14 into an artery, the plug and socket members 11 and 12 are simply rotated from the final or locked position back to the intermediate intermediate position. When a new position along the guidewire is established, the members 11 and 12 are returned to the locked position in which the device provides secure gripping of the guidewire 14 for both longitudinal and rotational movement.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A device for selective attachment to or detachment from a catheter guidewire or the like, and for selectively gripping the guidewire when attached to permit either longitudinal or rotational manipulation of the guidewire for purposes of steering the guidewire through a vessel, comprising:

a tubular housing means for receiving and retaining the guidewire comprising a longitudinal passageway therethrough and a radial slot extending from an outer surface to the passageway along the full length of said housing means, and further comprising first and second rotatably connected members which are rotatably operative such that when the members are rotated into a first position of alignment relative to each other the guidewire is adapted to be inserted into the passageway by slipping the guidewire through the slot, and such that when the members are rotated into a second position of alignment relative to each other the guidewire is secured both longitudinally and rotationally relative to the housing means; and retention and gripping means situated within said passageway and having one end anchored in the first member and another end anchored in the second member such that said retention and gripping means will urge and hold the first and second members together under compressive force, and said retention and gripping means securing the guidewire both longitudinally and rotationally relative to said housing means when the members are rotated into the second position.

2. A device as defined in claim 1 wherein said housing means comprises stop means for aligning said first and second members at said first position.

3. A device as defined in claim 2 wherein said housing means comprises first locking means for releasably securing the first and second members in the second position.

4. A device as defined in claim 3 wherein said members are operative so as to be rotated into a third position of alignment relative to each other such that the housing means is locked onto the guidewire but the housing means is not secured longitudinally and rotationally to the guidewire, and wherein said housing means comprises second locking means for releasably securing the first and second members in the third position.

5. A device as defined in claim 4 wherein said second locking means is disposed intermediate the stop means and the first locking means.

6. A device as defined in claim 1 wherein said first and second members comprise, respectively, first and second tubular members which are telescoped together, and wherein the longitudinal passageway is comprised of first and second passageways formed through each respective tubular member, and wherein the radial slot is comprised of first and second radial slots extending from an outer surface of the respective tubular member to the corresponding first and second passageways.

7. A device as defined in claim 6 wherein said retention and gripping means comprises an elastomeric member having first and second ends and an elongated body member, and wherein a first end of the elastomer member is anchored in an end of the first passageway in the first tubular member, the second end of the elastomeric member is anchored in an end of the second passageway in the second tubular member, and the body member is situated in the first and second passageways therebetween.

8. A device as defined in claim 7 wherein said housing means comprises means for twisting the body member as the first and second ends of the elastomeric member are rotated relative to one another by rotating said first and second tubular members into the second position, such that the body member is twisted about the guidewire so as to frictionally engage and secure the guidewire against longitudinal and rotational movement relative to the housing means, without bending the guidewire.

9. A device as defined in claim 8 wherein said housing means comprises stop means for aligning said first and second members at said first position.

10. A device as defined in claim 9 wherein said housing means comprises first locking means for releasably securing the first and second members in the second position.

11. A device as defined in claim 10 wherein said members are operative so as to be rotated into a third position of alignment relative to each other such that the housing means is locked onto the guidewire but the housing means is not secured longitudinally and rotationally to the guidewire, and wherein said housing means comprises second locking means for releasably securing the first and second members in the third position.

12. A device as defined in claim 11 wherein said second locking means is disposed intermediate the stop means and the first locking means.

13. A device as defined in claim 1 further comprising an indicator means for providing visual verification of when said first and second members are rotated to the second position of alignment.

14. A device as defined in claims 4 or 12 further comprising first and second indicator means for providing visual verification of when said first and second members are rotated to the second and third positions of alignment, respectively, relative to one another.

15. A device as defined in claims 1 or 13 further comprising rotational indicator means for providing visual direction as to the direction of rotation of said first and second members relative to one another.

16. A device for selective attachment to or detachment from a catheter guidewire or the like, and for selectively gripping the guidewire when attached to permit either longitudinal or rotational manipulation of the guidewire for purposes of steering the guidewire through a vessel, comprising:

a tubular housing means for receiving and retaining the guidewire comprising a longitudinal passageway therethrough and a radial slot extending from an outer surface to the passageway along the full length of said housing means, and further comprising first and second rotatably connected members which are rotatably operative such that when the members are rotated into a first position of alignment relative to each other the guidewire is adapted to be inserted into the passageway by slipping the guidewire through the slot, and such that when the members are rotated into a second position of alignment relative to each other the guidewire is locked within the passageway so that the housing means cannot fall off the guidewire but the guidewire is not secured longitudinally that when the members are rotated into a third position of alignment the guidewire is secured both longitudinally and rotationally relative to the housing means;

said housing means further comprising stop means for aligning said first and second members at said first position, first locking means for releasably securing the first and second members in the second position, and second locking means for releasably securing the first and second members in the third position; and elastomeric retention and gripping means situated within said passageway and having one end anchored in the first member and another end anchored in the second member such that said elastomeric retention and gripping means will urge and hold the first and second members together under compressive force, and said elastomeric retention and gripping means securing the guidewire both longitudinally and rotationally relative to said housing means when the members are rotated into the third position.

17. A device as defined in claim 16 wherein said first and second members comprise, respectively, first and second tubular members which are telescoped together, and wherein the longitudinal passageway is comprised of first and second passageways formed through each respective tubular member, and wherein the radial slot is comprised of first and second radial slots extending from an outer surface of the respective tubular member to the corresponding first and second passageways.

18. A device as defined in claim 17 wherein the elastomeric retention and gripping means comprises an elastomeric member having first and second ends and an elongated body member, and wherein a first end of the elastomeric member is anchored in an end of the first passageway in the first tubular member, the second end of the elastomeric member is anchored in an end of the second passageway in the second tubular member, and the body member is situated in the first and second passageways therebetween.

19. A device as defined in claim 18 wherein said housing means comprises means for twisting the body member as the first and second ends of the elastomeric member are rotated relative to one another by rotating said first and second tubular members into the third position, such that the body member is twisted about the guidewire so as to frictionally engage and secure the guidewire against longitudinal and rotational movement relative to the housing means, without bending the guidewire.

20. A device as defined in claims 1 or 19 further comprising first and second indicator means for providing visual verification of when said first and second members are rotated to the second and third positions of alignment, respectively, relative to one another.

21. A device as defined in claim 20 further comprising rotational indicator means for providing visual direction as to the direction of rotation of said first and second members relative to one another.

22. A device for selective attachment to or detachment from a catheter guidewire or the like, and for selectively gripping the guidewire when attached to permit either longitudinal or rotational manipulation of the guidewire for purposes of steering the guidewire through a vessel, comprising:

a first tubular member having a head, a cylindrical shank with a first central axis and extending from the head, and a passage extending longitudinally through the member, the passage having a second central axis which is offset from the first axis, the passage further having an enlarged portion at its end within the head;

a second tubular member with first and second ends, and having a cylindrical bore extending from the first end to a base surface spaced from the second end, the bore being dimensioned to receive the cylindrical shank in coaxial telescoping fashion to place the first and second members in rotatable engagement; the second member having a passage extending longitudinally from the second end to the base surface, the passage further having an enlarged portion at its end adjacent the second surface;

the first and second members each having a slot extending longitudinally therethrough and extending radially from each respective passage to a respective outer surface of the member; the slots of the members being aligned when the members are in a first rotational position, and misaligned when the members are relatively rotated to a second or a third position;

an elongated elastomeric member having a central shank with enlarged ends, the elastomer member being fitted in the passages of the first and second members with the enlarged ends seated in said enlarged portions to place the central shank in tension and thereby to urge the first and second members together;

the first and second members defining a stop means for limiting relative rotation therebetween to movement from the first to the second or third positions, and vice versa;

whereby the assembly can be moved laterally over the guidewire when the members are in the first position to place the guidewire in the passages against the elastomeric member, and rotation of the tubular members to the second position traps the guidewire within the assembly but without securing the guidewire against longitudinal and rotational movement relative to the assembly, and rotation of the tubular members to the third position traps the guidewire within the assembly and secures the guidewire against longitudinal and rotational movement relative to the assembly.

23. A device as defined in claim 22 further comprising means for twisting the central shank of the elastomeric member as the enlarged ends thereof are rotated relative to one another by rotating the tubular members to the third position, thereby frictionally engaging and securing the guidewire against longitudinal and rotational movement relative to the assembly, without bending the guidewire.

24. A device as defined in claim 23 further comprising first locking means for releasably securing the first and second tubular members in the second position.

25. A device as defined in claim 24 further comprising second locking means for releasably securing the first and second tubular members in the third position.

26. A device as defined in claim 25 further comprising first and second indicator means for providing visual verification of when said first and second members are rotated to the second and third positions of alignment, respectively, relative to one another.

27. A device as defined in claim 26 further comprising rotational indicator means for providing visual direction as to the direction of rotation of said first and second members relative to one another.

* * * * *

UNITED STATES PATENT AND TRADEMARK OFFICE
CERTIFICATE OF CORRECTION

PATENT NO. : 5,219,332
DATED : June 15, 1993
INVENTOR(S) : ARLIN D. NELSON et al.

It is certified that error appears in the above-indentified patent and that said Letters Patent is hereby corrected as shown below:

Col. 6, line 54, "permitting" should be --permits--

Column 9, line 54, after "longitudinally" insert --so--

Signed and Sealed this

Twelfth Day of April, 1994

Attest:

BRUCE LEHMAN

*Commissioner of Patents and Trademarks*

*Attesting Officer*